US012226622B2

(12) United States Patent
Kheradvar et al.

(10) Patent No.: US 12,226,622 B2
(45) Date of Patent: Feb. 18, 2025

(54) PERCUTANEOUS MEDICAL DEVICE DELIVERY SYSTEM

(71) Applicant: THE REGENTS OF THE UNIVERSITY OF CALIFORNIA, Oakland, CA (US)

(72) Inventors: Arash Kheradvar, Irvine, CA (US); Gregory S. Kelley, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 533 days.

(21) Appl. No.: 17/612,374

(22) PCT Filed: May 18, 2020

(86) PCT No.: PCT/US2020/033466
§ 371 (c)(1),
(2) Date: Nov. 18, 2021

(87) PCT Pub. No.: WO2020/236750
PCT Pub. Date: Nov. 26, 2020

(65) Prior Publication Data
US 2022/0296879 A1 Sep. 22, 2022

Related U.S. Application Data

(60) Provisional application No. 62/850,393, filed on May 20, 2019.

(51) Int. Cl.
*A61M 60/865* (2021.01)
*A61M 60/191* (2021.01)
(Continued)

(52) U.S. Cl.
CPC ........ *A61M 60/191* (2021.01); *A61M 60/289* (2021.01); *A61M 60/47* (2021.01);
(Continued)

(58) Field of Classification Search
CPC .. A61M 60/865; A61M 60/47; A61M 60/289; A61M 60/191
See application file for complete search history.

(56) References Cited

U.S. PATENT DOCUMENTS 5,879,375 A 3/1999 Larson, Jr. et al.
6,309,379 B1 10/2001 Willard et al.
(Continued)

FOREIGN PATENT DOCUMENTS

WO WO2020236750 A1 11/2020

OTHER PUBLICATIONS

Zegdi et al. "Evidence of leaflet injury during percutaneous aortic valve deployment." European journal of cardio-thoracic surgery 40.1 (2011): 257-260.
(Continued)

*Primary Examiner* — Rex R Holmes
*Assistant Examiner* — Jennifer L Ghand
(74) *Attorney, Agent, or Firm* — NGUYEN TARBET IP LAW

(57) ABSTRACT

A medical device delivery system including a delivery sheath that includes an internal lumen, and a plurality of delivery arms contained within the internal lumen of the delivery sheath and extending along a longitudinal axis of the internal lumen of the delivery sheath, wherein distal ends of the delivery arms include fasteners configured to engage with a basal structure of a medical device and a apical structure of the medical device, wherein the delivery arms are attached to delivery arm controls that are configured to advance the delivery arms and the medical device attached thereto out from a distal end of the delivery sheath, and removable release wires or release lines configured to engage with the fasteners to hold the basal structure and the apical structure in place at the fasteners. Also disclosed are
(Continued)

methods of delivering a medical device to a subject including inserting a distal end of the medical device delivery system through an incision in the skin of subject, and deploying a medical device engaged with the delivery arms of the medical delivery system to within the body of the subject.

7 Claims, 13 Drawing Sheets

(51) Int. Cl.
    *A61M 60/289*     (2021.01)
    *A61M 60/47*     (2021.01)
    *A61M 60/495*     (2021.01)
    *A61M 60/861*     (2021.01)

(52) U.S. Cl.
    CPC ........ *A61M 60/495* (2021.01); *A61M 60/861* (2021.01); *A61M 60/865* (2021.01)

(56) References Cited

U.S. PATENT DOCUMENTS

| | | | |
|---|---|---|---|
| 6,984,201 | B2 | 1/2006 | Khaghani et al. |
| 7,491,170 | B2 | 2/2009 | Gharib |
| 7,524,298 | B2 | 4/2009 | Gharib et al. |
| 7,749,152 | B2 | 7/2010 | Gharib et al. |
| 7,883,325 | B2 | 2/2011 | Kheradvar et al. |
| 8,075,471 | B2 | 12/2011 | Trumble |
| 8,133,270 | B2 | 3/2012 | Kheradvar et al. |
| 8,794,937 | B2 | 8/2014 | Kheradvar et al. |
| 9,656,009 | B2 | 5/2017 | Kheradvar et al. |
| 10,835,713 | B2 | 11/2020 | Homsy et al. |
| 11,413,144 | B2 | 8/2022 | Rothstein et al. |
| 2001/0041850 | A1 | 11/2001 | Brenneman et al. |
| 2001/0047122 | A1 | 11/2001 | Vanden Hoek et al. |
| 2002/0045799 | A1 | 4/2002 | Lau et al. |
| 2005/0240200 | A1 | 10/2005 | Bergheim |
| 2005/0278010 | A1 | 12/2005 | Richardson |
| 2006/0020377 | A1 | 1/2006 | Goetz et al. |
| 2006/0043191 | A1 | 3/2006 | Patel et al. |
| 2006/0167334 | A1 | 7/2006 | Anstadt et al. |
| 2006/0259137 | A1 | 11/2006 | Artof et al. |
| 2007/0005131 | A1 | 1/2007 | Taylor |
| 2007/0015958 | A1* | 1/2007 | Lau .................. A61B 17/00234 600/37 |
| 2007/0021826 | A1 | 1/2007 | Case et al. |
| 2007/0038291 | A1 | 2/2007 | Case et al. |
| 2007/0185369 | A1* | 8/2007 | Mirhoseini ......... A61M 60/289 607/9 |
| 2007/0197859 | A1 | 8/2007 | Schaer et al. |
| 2007/0203560 | A1 | 8/2007 | Forster et al. |
| 2007/0239254 | A1 | 10/2007 | Chia et al. |
| 2008/0046016 | A1 | 2/2008 | Ben-David et al. |
| 2008/0228266 | A1 | 9/2008 | McNamara et al. |
| 2009/0036730 | A1 | 2/2009 | Criscione et al. |
| 2009/0131740 | A1 | 5/2009 | Gharib |
| 2009/0281619 | A1 | 11/2009 | Le et al. |
| 2011/0019886 | A1 | 1/2011 | Mizuno |
| 2011/0144690 | A1 | 6/2011 | Bishop et al. |
| 2012/0165916 | A1 | 6/2012 | Jordan |
| 2012/0283820 | A1 | 11/2012 | Tseng et al. |
| 2013/0030519 | A1 | 1/2013 | Tran et al. |
| 2013/0046377 | A1 | 2/2013 | Cohn |
| 2013/0110895 | A1 | 5/2013 | Valentino et al. |
| 2013/0243288 | A1 | 9/2013 | Goto |
| 2013/0310923 | A1 | 11/2013 | Kheradvar et al. |
| 2014/0107768 | A1 | 4/2014 | Venkatsubramanian |
| 2014/0228943 | A1 | 8/2014 | Stigall et al. |
| 2014/0316518 | A1 | 10/2014 | Kheradvar et al. |
| 2014/0336743 | A1 | 11/2014 | Zotz |
| 2014/0350350 | A1 | 11/2014 | Imagawa et al. |
| 2015/0057488 | A1 | 2/2015 | Yomtov |
| 2016/0045316 | A1 | 2/2016 | Braido et al. |
| 2016/0206798 | A1 | 7/2016 | Williams et al. |
| 2017/0080137 | A1* | 3/2017 | Criscione ............ A61M 60/148 |
| 2017/0086974 | A1 | 3/2017 | Lashinski et al. |
| 2017/0296055 | A1 | 10/2017 | Gardner et al. |
| 2017/0319333 | A1 | 11/2017 | Tegels et al. |
| 2018/0214266 | A1* | 8/2018 | Paul ...................... A61F 2/2427 |
| 2018/0245243 | A1 | 8/2018 | Krieger et al. |
| 2018/0300875 | A1 | 10/2018 | Imasugi |
| 2019/0060542 | A1* | 2/2019 | Altman ............... A61M 60/165 |
| 2019/0133764 | A1 | 5/2019 | Carr et al. |
| 2019/0282360 | A1 | 9/2019 | Colavito et al. |
| 2019/0336280 | A1 | 11/2019 | Naor et al. |
| 2020/0078002 | A1 | 3/2020 | Hacohen et al. |
| 2020/0226422 | A1 | 7/2020 | Li et al. |
| 2021/0275299 | A1 | 9/2021 | Peterson et al. |
| 2022/0183830 | A1 | 6/2022 | Tseng et al. |
| 2022/0233307 | A1 | 7/2022 | Tuval |

OTHER PUBLICATIONS

De Buhr et al. "Impairment of pericardial leaflet structure from balloon-expanded valved stents." The Journal of Thoracic and Cardiovascular Surgery 143.6 (2012): 1417-1421.

Ong, Sea Hing, Ralf Mueller, and Stein Iversen. "Early calcific degeneration of a CoreValve transcatheter aortic bioprosthesis." European heart journal 33.5 (2012): 586-586.

Harbaoui et al. "Early Edwards Sapien valve degeneration after transcatheter aortic valve replacement." JACC: Cardiovascular Interventions 9.2 (2016): 198-199.

Webb, John G., and Danny Dvir. "Is transcatheter aortic valve replacement a durable therapeutic strategy ?. " JACC: Cardiovascular Interventions 8.8 (2015): 1092-1094.

Sinha, Aditi, Oleksandr Barannyk, and Arash Kheradvar. "Crimp induced leaflet damage and calcification of transcatheter heart valves." Cardiology 134.2 (2016): 170-171.

Makkar, Raj R., and Tarun Chakravarty. "Transcatheter aortic valve thrombosis: new problem, new insights." JACC: Cardiovascular Interventions 10.7 (2017): 698-700.

Bush, Charles H., John D. Reith, and Suzanne S. Spanier. "Mineralization in Musculoskeletal Leiomyosarcoma: Radiologic—Pathologic Correlation." American Journal of Roentgenology 180.1 (2003): 109-113.

Otto, C. M. "Calcification of bicuspid aortic valves." Heart 88.4 (2002): 321-322.

Alavi, S. Hamed, Elliott M. Groves, and Arash Kheradvar. "The effects of transcatheter valve crimping on pericardial leaflets." The Annals of thoracic surgery 97.4 (2014): 1260-1266.

Dasi, Lakshmi P., et al. "On the mechanics of transcatheter aortic valve replacement." Annals of biomedical engineering 45.2 (2017): 310-331.

Delogne, Christophe, et al. "Characterization of the calcification of cardiac valve bioprostheses by environmental scanning electron microscopy and vibrational spectroscopy." Journal of microscopy 228.1 (2007): 62-77.

Schoen, Frederick J., Jack W. Tsao, and Robert J. Levy. "Calcification of bovine pericardium used in cardiac valve pioprostheses. Implications for the mechanisms of bioprosthetic tissue mineralization." The American journal of pathology 123.1 (1986): 134.

Bertazzo et al. "Nano-analytical electron microscopy reveals fundamental insights into human cardiovascular tissue calcification." Nature materials 12.6 (2013): 576-583.

Schoen, Frederick J., and Robert J. Levy. "Calcification of tissue heart valve substitutes: progress toward understanding and prevention." The Annals of thoracic surgery 79.3 (2005): 1072-1080.

Khoffi et al. "Transcatheter fiber heart valve: effect of crimping on material performances." Journal of Biomedical Materials Research Part B: Applied Biomaterials 103.7 (2015): 1488-1497.

Arora et al. "Early transcatheter valve prosthesis degeneration and future ramifications." Cardiovascular Diagnosis and Therapy 7.1 (2017): 1.

Chhatriwalla et al. "Bioprosthetic valve fracture improves the hemodynamic results of valve-in-valve transcatheter aortic valve replacement." Circulation: Cardiovascular Interventions 10.7 (2017): e005216.

(56) References Cited

OTHER PUBLICATIONS

Sathananthan et al. "Valve-in-valve transcatheter aortic valve replacement and bioprosthetic valve fracture comparing different transcatheter heart valve designs: an ex vivo bench study." JACC: Cardiovascular Interventions 12.1 (2019): 65-75.
Yuan S-M, Mishaly D, Shinfeld A, Raanani E. Right ventricular outflow tract reconstruction: Valved conduit of choice and clinical outcomes. Journal of Cardiovascular Medicine. 2008;9:327-337.
Gatzoulis MA, Balaji S, Webber SA, Siu SC, Hokanson JS, Poile C, Rosenthal M, Nakazawa M, Moller JH, Gillette PC, Webb GD, Redington AN. Risk factors for arrhythmia and sudden cardiac death late after repair of tetralogy of fallot: A multicentre study. The Lancet. 2000;356:975-981.
Texakalidis P, Giannopoulos S, Kokkinidis DG, Lanzino G. Effect of open- vs closed-cell stent design on periprocedural outcomes and restenosis after carotid artery stenting: A systematic review and comprehensive meta-analysis. Journal of Endovascular Therapy. 2018;25:523-533.
Jalal Z, Galmiche L, Lebeaux D, Villemain O, Brugada G, Patel M, Ghigo J-M, Beloin C, Boudjemline Y. Selective propensity of bovine jugular vein material to bacterial adhesions: An in-vitro study. International Journal of Cardiology. 2015;198:201-205.
Richardt, Doreen, Thorsten Hanke, and Hans-Hinrich Sievers. "Two cases of heart failure after implantation of a CoreValve prosthesis." The New England journal of medicine 372.11 (2015): 1079-1080.
Thielmann, M., et al. "Current developments in transcatheter aortic valve implantation techniques." Herz 36.8 (2011):696-705.
Svensson, Lars G., et al. "United States feasibility study of transcatheter insertion of a stented aortic valve by the left ventricular apex." The Annals of thoracic surgery 86.1 (2008): 46-55.
Pislaru SV, et al. 2014 Progress in Cardiovascular Diseases 57:32-46.
Bartel T, et al. 2011 Journal of the American Society of Echocardiography 24:966-975.
Okabe, Teruo, et al. "The predictive value of computed tomography calcium scores: a comparison with quantitative volumetric intravascular ultrasound." Cardiovascular Revascularization Medicine 10.1 (2009): 30-35.
Beebe, Hugh G. "Imaging modalities for aortic endografting." Journal of Endovascular Therapy 4.2 (1997): 111-123.
Kawase, Yoshiaki, et al. "In vivo volumetric analysis of coronary stent using optical coherence tomography with a novel balloon occlusion-flushing catheter: a comparison with intravascular ultrasound." Ultrasound in medicine & biology 31.10 (2005): 1343-1349.
Ávila, P., et al. "IVUS guidance in percutaneous closure of aortic paraprosthetic leak." Cardiovascular intervention and therapeutics 27.2 (2012): 137-139.
Alboliras, Ernerio T., and Ziyad M. Hijazi. "Comparison of costs of intracardiac echocardiography and transesophageal echocardiography in monitoring percutaneous device closure of atrial septal defect in children and adults." The American journal of cardiology 94.5 (2004): 690-692.
Falahatpisheh, Ahmad, and Arash Kheradvar. "High-speed particle image velocimetry to assess cardiac fluid dynamics in vitro: From performance to validation." European Journal of Mechanics-B/Fluids 35 (2012): 2-8.
Kiefer, Philipp, et al. "Crimping may affect the durability of transcatheter valves: an experimental analysis." The Annals of thoracic surgery 92.1 (2011): 155-160.
Van Steenberghe, Mathieu, et al. "Early transcatheter aortic valve degeneration in the young." International Journal of Cardiology 222 (2016): 786-787.
Pascual, Isaac, Pablo Avanzas, and César Moris. "Degenerative pattern of a percutaneous aortic valve." Revista espanola de cardiologia (English ed.) 70.9 (2017): 772.
Kapolos et al. "Model experimental system for investigation of heart valve calcification in vitro." Journal of biomedical materials research 38.3 (1997): 183-190.
Krings et al. "Development of a new combined test setup for accelerated dynamic pH-controlled in vitro calcification of porcine heart valves." The International Journal of Artificial Organs 32.11 (2009): 794-801.
Tertti, Risto, et al. "Comparison of calcium phosphate product values using measurement of plasma total calcium and serum ionized calcium." Hemodialysis International 11.4 (2007): 411-416.
Cheng, Ching-Li, et al. "Ex vivo assessment of valve thickness/calcification of patients with calcific aortic stenosis in relation to in vivo clinical outcomes." Journal of the Mechanical Behavior of Biomedical Materials 74 (2017): 324-332.
Foroutan, Farid, et al. "Structural valve deterioration after transcatheter aortic valve implantation." Heart 103.23 (2017):1899-1905.
Leon MB, et al. "Transcatheter aortic-valve implantation for aortic stenosis in patients who cannot undergo surgery" 2010 The New England Journal of Medicine 363:1597-1607.
Mack, Michael J. "Does transcatheter aortic valve implantation mean the end of surgical aortic valve replacement ?. " Texas Heart Institute Journal 37.6 (2010): 658.
Cribier et al. "Percutaneous transcatheter implantation of an aortic valve prosthesis for calcific aortic stenosis: first human case description." Circulation 106.24 (2002): 3006-3008.
Makkar, et al. "Transcatheter aortic-valve replacement for inoperable severe aortic stenosis." New England Journal of Medicine 366.18 (2012): 1696-1704.
Geisbüsch et al. "Incidence and management of CoreValve dislocation during transcatheter aortic valve implantation." Circulation: Cardiovascular Interventions 3.6 (2010): 531-536.
Thomas et al. "Thirty-day results of the SAPIEN aortic Bioprosthesis European Outcome (Source) Registry: a European registry of transcatheter aortic valve implantation using the Edwards Sapien valve." Circulation 122.1 (2010): 62-69.
Ussia, et al. "The valve-in-valve technique for treatment of aortic bioprosthesis malposition: an analysis of incidence and 1-year clinical outcomes from the Italian CoreValve registry." Journal of the American College of Cardiology 57.9 (2011): 1062-1068.
Masson et al. "Transcatheter aortic valve implantation: review of the nature, management, and avoidance of procedural complications." JACC: Cardiovascular Interventions 2.9 (2009): 811-820.
Webb, John G., et al. "Transcatheter valve-in-valve implantation for failed bioprosthetic heart valves." Circulation 121.16 (2010): 1848-1857.
Gurvitch et al. "Transcatheter valve-in-valve implantation for failed surgical bioprosthetic valves." Journal of the American College of Cardiology 58.21 (2011): 2196-2209.
Groves et al. "The effects of positioning of transcatheter aortic valve on fluid dynamics of the aortic root." ASAIO Journal (American Society for Artificial Internal Organs: 1992) 60.5 (2014): 545.
Su, Jimmy Li-Shin, Bo Wang, and Stanislav Y. Emelianov. "Photoacoustic imaging of coronary artery stents." Optics Express 17.22 (2009): 19894-19901.
Elgort, et al. "Image-guided and-monitored renal artery stenting using only MRI." Journal of Magnetic Resonance Imaging: An Official Journal of the International Society for Magnetic Resonance in Medicine 23.5 (2006): 619-627.
De Heer et al. "Multimodality imaging throughout transcatheter aortic valve implantation." Future Cardiology 8.3 (2012): 413-424.
Jilaihawi et al. "Cross-sectional computed tomographic assessment improves accuracy of aortic annular sizing for transcatheter aortic valve replacement and reduces the incidence of paravalvular aortic regurgitation." Journal of the American College of Cardiology 59.14 (2012): 1275-1286.
Willson et al. "3-dimensional aortic annular assessment by multidetector computed tomography predicts moderate or severe paravalvular regurgitation after transcatheter aortic valve replacement: a multicenter retrospective analysis." Journal of the American College of Cardiology 59.14 (2012): 1287-1294.
Jilaihawi et al. "A revised methodology for aortic-valvar complex calcium quantification for transcatheter aortic valve implantation." Eur Heart J Cardiovasc Imaging. Dec. 2014; 15(12):1324-32.
White et al. "The role of cinefluoroscopy and intravascular ultrasonography in evaluating the deployment of experimental endovascular prostheses." Journal of vascular surgery 21.3 (1995): 365-374.

(56) References Cited

OTHER PUBLICATIONS

Moss et al. "Role of echocardiography in percutaneous aortic valve implantation." JACC: Cardiovascular Imaging 1.1 (2008): 15-24.
Naqvi, Tasneem Z. "Echocardiography in percutaneous valve therapy." JACC: Cardiovascular Imaging 2.10 (2009): 1226-1237.
Dumont et al. "Feasibility of transapical aortic valve implantation fully guided by transesophageal echocardiography." The Journal of Thoracic and Cardiovascular Surgery 138.4 (2009): 1022-1024.
Jánosi et al. "Guidance of percutaneous transcatheter aortic valve implantation by real-time three-dimensional transesophageal echocardiography-A single-center experience." Minimally Invasive Therapy & Allied Technologies 18.3 (2009): 142-148.
Bartel et al. "Intracardiac echocardiography for guidance of transcatheter aortic valve implantation under monitored sedation: a solution to a dilemma?. " European Heart Journal-Cardiovascular Imaging 17.1 (2016): 1-8.
Sengupta et al. "Transthoracic echocardiography guidance for TAVR under monitored anesthesia care." Cardiovascular Imaging 8.3 (2015): 379-380.
Choi et al. "Relationship between coronary artery calcium score by multidetector computed tomography and plaque components by virtual histology intravascular ultrasound." Journal of Korean medical science 26.8 (2011): 1052-1060.
Kpodonu, Jacques, Venkatesh G. Ramaiah, and Edward B. Diethrich. "Intravascular ultrasound imaging as applied to the aorta: a new tool for the cardiovascular surgeon." The Annals of thoracic surgery 86.4 (2008): 1391-1398.
Mintz et al. "American College of Cardiology clinical expert consensus document on standards for acquisition, measurement and reporting of intravascular ultrasound studies (ivus) a report of the american college of cardiology task force on clinical expert consensus documents developed in collaboration with the european society of cardiology endorsed by the society of cardiac angiography and interventions." Journal of the American College of Cardiology 37.5 (2001) :1748-1492.
Ferrari et al. "Imaging for trans-catheter pulmonary stent-valve implantation without angiography: role of intravascular ultrasound." European journal of cardio-thoracic surgery 40.2 (2011): 522-524.
Mathur, S. K., and Pooja Singh. "Transoesophageal echocardiography related complications." Indian Journal of Anaesthesia 53.5 (2009): 567.
Jánosi et al. "Quantitative analysis of aortic valve stenosis and aortic root dimensions by three-dimensional echocardiography in patients scheduled for transcutaneous aortic valve implantation." Current cardiovascular imaging reports 7.11 (2014): 1-9.
Maragiannis, Dimitrios, and Stephen H. Little. "Interventional imaging: the role of echocardiography." Methodist DeBakey cardiovascular journal 10.3 (2014): 172.
Klein, Andrew A., Nikolas J. Skubas, and Joerg Ender. "Controversies and complications in the perioperative management of transcatheter aortic valve replacement." Anesthesia & Analgesia 119.4 (2014): 784-798.
Klein et al. "Economic analysis of a transesophageal echocardiography-guided approach to cardioversion of patients with atrial fibrillation: the Acute economic data at eight weeks." Journal of the American College of Cardiology 43.7 (2004): 1217-1224.
Roy et al. "First-in-man use of aortic valve ultrasound for assessment of aortic valve anatomy pre-and post-transcatheter aortic valve implantation." JACC: Cardiovascular Interventions 6.6 (2013): 634-635.
Kheradvar et al. "Emerging trends in heart valve engineering: Part IV. Computational modeling and experimental studies." Annals of biomedical engineering 43.10 (2015): 2314-2333.
Kahlert et al. "Towards real-time cardiovascular magnetic resonance guided transarterial CoreValve implantation: in vivo evaluation in swine." Journal of Cardiovascular Magnetic Resonance 14.1 (2012): 1-15.
Kapadia et al. "Imaging for transcatheter valve procedures." Current problems in cardiology 35.5 (2010): 228-276.

Kheradvar, Arash, and Morteza Gharib. "On mitral valve dynamics and its connection to early diastolic flow." Annals of biomedical engineering 37.1 (2009): 1-13.
Kheradvar et al. "An in vitro study of changing profile heights in mitral bioprostheses and their influence on flow." Asaio Journal 52.1 (2006): 34-38.
Kheradvar, Arash, Michele Milano, and Morteza Gharib. "Correlation between vortex ring formation and mitral annulus dynamics during ventricular rapid filling." Asaio Journal 53.1 (2007): 8-16.
Tsukui et al. "Cerebrovascular accidents in patients with a ventricular assist device." The Journal of thoracic and cardiovascular surgery 134.1 (2007): 114-123.
Kirklin et al. "Fifth Intermacs annual report: risk factor analysis from more than 6,000 mechanical circulatory support patients." The Journal of heart and lung transplantation 32.2 (2013): 141-156.
Starling et al. "Unexpected abrupt increase in left ventricular assist device thrombosis." New England Journal of Medicine 370.1 (2014): 33-40.
Kirklin et al. "Interagency Registry for Mechanically Assisted Circulatory Support (Intermacs) analysis of pump thrombosis in the HeartMate II left ventricular assist device." The Journal of Heart and Lung Transplantation 33.1 (2014): 12-22.
Rigatelli, Gianluca, Francesco Santini, and Giuseppe Faggian. "Past and present of cardiocirculatory assist devices: a comprehensive critical review." Journal of Geriatric Cardiology: JGC 9.4 (2012): 389.
Almond, Christopher S. "The FDA review process for cardiac medical devices in children: a review for the clinician." Progress in pediatric cardiology 33.2 (2012): 105-109.
Grosberg, Anna, Morteza Gharib, and Arash Kheradvar. "Effect of fiber geometry on pulsatile pumping and energy expenditure." Bulletin of mathematical biology 71.7 (2009): 1580-1598.
Leon et al. "Transcatheter or surgical aortic-valve replacement in intermediate-risk patients." New England Journal of Medicine 374.17 (2016): 1609-1620.
Dvir et al. "Standardized definition of structural valve degeneration for surgical and transcatheter bioprosthetic aortic valves." Circulation 137.4 (2018): 388-399.
Kheradvar, Arash, et al. "Emerging trends in heart valve engineering: Part II. Novel and standard technologies for aortic valve replacement." Annals of biomedical engineering 43.4 (2015): 844-857.
Best, Kate E., and Judith Rankin. "Long-term survival of individuals born with congenital heart disease: a systematic review and meta-analysis." Journal of the American Heart Association 5.6 (2016): e002846.
Hoffman et al. "The incidence of congenital heart disease." Journal of the American college of cardiology 39.12 (2002): 1890-1900.
Dolk et al. "Congenital heart defects in Europe: prevalence and perinatal mortality, 2000 to 2005." Circulation 123.8 (2011): 841-849.
Oster, Matthew E., et al. "Temporal Trends in Survival Among Infants With Critical Congenital Heart Defects." Pediatrics 131.5 (2013): e1502-e1508.
Reller et al. "Prevalence of Congenital Heart Defects in Metropolitan Atlanta, 1998-2005." The Journal of pediatrics 153.6 (2008): 807.
Gilboa et al. "Congenital heart defects in the United States: estimating the magnitude of the affected population in 2010." Circulation 134.2 (2016): 101-109.
Liu et al. "Global birth prevalence of congenital heart defects 1970-2017: updated systematic review and meta-analysis of 260 studies." International journal of epidemiology 48.2 (2019): 455-463.
Davlouros et al. "The right ventricle in congenital heart disease." Heart 92 (2006): 127-i38.
Cho, Young Kuk, and Jae Sook Ma. "Right ventricular failure in congenital heart disease." Korean journal of pediatrics 56.3 (2013): 101.
Voelkel, et al. "Right ventricular function and failure: report of a National Heart, Lung, and Blood Institute working group on cellular and molecular mechanisms of right heart failure." Circulation 114.17 (2006): 1883-1891.

(56) References Cited

OTHER PUBLICATIONS

Haddad et al. "Right ventricular function in cardiovascular disease, part I: anatomy, physiology, aging, and functional assessment of the right ventricle." Circulation 117.11 (2008): 1436-1448.
Corno, Antonio F. "Pulmonary valve regurgitation: Neither interventional nor surgery fits all." Frontiers in Pediatrics 6 (2018): 169.
Martin et al. "Safety and feasibility of melody transcatheter pulmonary valve replacement in the native right ventricular putflow tract: a multicenter pediatric heart network scholar study." JACC: Cardiovascular Interventions 11.16 (2018): 1642-1650.
Zheng et al. "Long-term outcome of correction of tetralogy of Fallot in 56 adult patients." Chinese medical journal 126.19 (2013): 3675-3679.
Mitropoulos, et al. "Pulmonary valve replacement in patients with corrected tetralogy of Fallot." Journal of Cardiovascular and Thoracic Research 9.2 (2017): 71.
Warner et al. "Expanding the indications for pulmonary valve replacement after repair of tetralogy of Fallot." The Annals of thoracic surgery 76.4 (2003): 1066-1071.
Stern, Menachem, Matthew B. Pinson, and Arvind Murugan. "The complexity of folding self-folding origami." Physical Review X 7.4 (2017): 041070.
Peraza Hernandez, E. A., D. J. Hartl, and D. C. Lagoudas. "Design and simulation of origami structures with smooth folds." Proceedings of the Royal Society A: Mathematical, Physical and Engineering Sciences 473.2200 (2017): Jul. 16, 2016.
Schlickenrieder, Wolfram. "Nets of polyhedra." Master's Thesis, Technische Universität Berlin (1997).
Krankenberg et al. "Self-expanding versus balloon-expandable stents for iliac artery occlusive disease: the randomized Ice trial." JACC: Cardiovascular Interventions 10.16 (2017): 1694-1704.
Kheradvar et al. "Proof of concept of Foldavalve, a novel 14 Fr totally repositionable and retrievable transcatheter aortic valve." EuroIntervention: journal of EuroPCR in collaboration with the Working Group on Interventional Cardiology of the European Society of Cardiology 11.5 (2015): 591-596.
Yi et al. "Bioinspired reversible hydrogel adhesives for wet and underwater surfaces." Journal of Materials Chemistry B 6.48 (2018): 8064-8070.
Zhao et al. "Bio-inspired reversible underwater adhesive." Nature communications 8.1 (2017): 1-8.
Lee, Haeshin, Bruce P. Lee, and Phillip B. Messersmith. "A reversible wet/dry adhesive inspired by mussels and geckos." Nature 448.7151 (2007): 338-341.
Cho et al. "Intrinsically reversible superglues via shape adaptation inspired by snail epiphragm." Proceedings of the National Academy of Sciences 116.28 (2019): 13774-13779.
Cools et al. "Medium term follow-up after percutaneous pulmonary valve replacement with the Melody® valve." IJC Heart & Vasculature 7 (2015): 92-97.
Zareian et al. "Effect of stent crimping on calcification of transcatheter aortic valves." Interactive cardiovascular and thoracic surgery 29.1 (2019): 64-73.
Lepidi et al. "Quantitative histological examination of bioprosthetic heart valves." Clinical infectious diseases 42.5 (2006): 590-596.
Lepidi et al. "Quantitative analysis of valvular lesions during Bartonella endocarditis." American journal of clinical pathology 114.6 (2000): 880-889.
Sellers et al. "Transcatheter aortic heart valves: histological analysis providing insight to leaflet thickening and structural valve degeneration." JACC: Cardiovascular Imaging 12.1 (2019): 135-145.
Martin, Caitlin, and Wei Sun. "Biomechanical characterization of aortic valve tissue in humans and common animal models." Journal of biomedical materials research. Part A 100.6 (2012).
Jiao et al. "Measurements of the Effects of Decellularization on Viscoelastic Properties of Tissues in Ovine, Baboon, and Human Heart Valves." Tissue Engineering. Part A 18.3-4 (2012): 423.
White et al. "Heart valve collagens: cross-species comparison using immunohistological methods." Journal of Heart Valve Disease 19.6 (2010): 766.
McCoy et al. "Sex-related differences in gene expression by porcine aortic valvular interstitial cells." PloS one 7.7 (2012): e39980.
Choo et al. "Development of an animal experimental model for a bileaflet mechanical heart valve prosthesis." Journal of Korean medical science 19.1 (2004): 37-41.
Capulli et al. "JetValve: Rapid manufacturing of biohybrid scaffolds for biomimetic heart valve replacement." Biomaterials 133 (2017): 229-241.
Ropcke et al. "Small intestinal submucosa tricuspid valve tube graft shows growth potential, remodelling and physiological valve function in a porcine model." Interactive CardioVascular and Thoracic Surgery 24.6 (2017): 918-924.
Yoon et al. "Outcomes of transcatheter mitral valve replacement for degenerated bioprostheses, failed annuloplasty rings, and mitral annular calcification." European heart journal 40.5 (2019): 441-451.
Guerrero et al. "1-year outcomes of transcatheter mitral valve replacement in patients with severe mitral annular calcification." Journal of the American College of Cardiology 71.17 (2018): 1841-1853.
Khan, Jaffar M., et al. "Anterior leaflet laceration to prevent ventricular outflow tract obstruction during transcatheter mitral valve replacement." Journal of the American College of Cardiology 73.20 (2019): 2521-2534.
Blanke et al. "Predicting LVOT obstruction in transcatheter mitral valve implantation: concept of the neo-LVOT." JACC: Cardiovascular Imaging 10.4 (2017): 482-485.
Khan et al. ""Rescue" Lampoon to Treat Transcatheter Mitral Valve Replacement—Associated Left Ventricular Outflow Tract Obstruction." JACC: Cardiovascular Interventions 12.13 (2019): 1283-1284.
Khan et al. "Lampoon to facilitate Tendyne transcatheter mitral valve replacement." JACC: Cardiovascular Interventions 11.19 (2018): 2014-2017.
Greenbaum et al. "Long or redundant leaflet complicating transcatheter mitral valve replacement: case vignettes that advocate for removal or reduction of the anterior mitral leaflet." Catheterization and Cardiovascular Interventions 92.3 (2018): 627-632.
Cantwell et al. "Techniques for automated local activation time annotation and conduction velocity estimation in cardiac mapping." Computers in biology and medicine 65 (2015): 229-242.
"Conventional Intracardiac Mapping Techniques"; https://thoracickey.com/conventional-intracardiac-mapping-techniques/; retrieved from web Jul. 1, 2024.
Clayton, Richard H., and Alexander V. Panfilov. "A guide to modelling cardiac electrical activity in anatomically detailed ventricles." Progress in biophysics and molecular biology 96.1-3 (2008): 19-43.
O'Shea et al. "ElectroMap: high-throughput open-source software for analysis and mapping of cardiac electrophysiology." Scientific reports 9.1 (2019): 1389.

\* cited by examiner

A

B

C

PERCUTANEOUS MEDICAL DEVICE DELIVERY SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field of the Invention

A delivery system for non-invasively implanting a medical device, such as a direct cardiac compression device that assists cardiac pumping function, in a subject.

Description of the Related Art

Methods of assisting cardiac pumping function are known in the art. Prior methods have provided assisted contraction around a heart transmitted helically (U.S. Pat. Nos. 7,883, 325, 8,794,937, and 9,656,009). There is a need for noninvasive implantation and deployment of whole-heart cardiac assist devices, for example in treating heart failure, such as congestive heart failure.

SUMMARY

We disclose a medical device delivery system to which is releasably attached a medical device, such as a direct cardiac compression device. In some examples, the direct cardiac compression device is a whole-heart assist device. The delivery system may be inserted between the patient's ribs and through an incision in the pericardium below the heart apex. Delivery arms are used to advance the direct cardiac compression device out of the delivery system sheath and to guide the medical device into position. In some examples, the direct cardiac compression device is a whole-heart assist device that comprises basal and apical structures that are interconnected to each other by helically-arranged fibers. The medical delivery system is used to place the whole-heart assist device in position around the heart. The whole-heart assist device externally wraps the heart and its structure, wherein the whole-heart assist device is expandable from a collapsed state to an expanded state.

Some embodiments relate to a medical device delivery system including:
  a delivery sheath that includes an internal lumen, and
  a plurality of delivery arms contained within the internal lumen of the delivery sheath and extending along a longitudinal axis of the internal lumen of the delivery sheath, wherein distal ends of the delivery arms include fasteners configured to engage with a basal structure of a medical device and a apical structure of the medical device, wherein the delivery arms are attached to delivery arm controls that are configured to advance the delivery arms and the medical device attached thereto out from a distal end of the delivery sheath, and
  removable release wires or release lines configured to engage with the fasteners to hold the basal structure and the apical structure in place at the fasteners.

In some examples, the medical device is a direct cardiac compression device engaged with the distal ends of the delivery arms, wherein the medical delivery system is configured to deliver the direct cardiac compression device into a thoracic cavity of a subject.

In some examples, the direct cardiac compression device includes an apical structure and a basal structure that are parallel to each other and flexibly connected to each other by a plurality of helically-arranged fibers spanning between the basal structure and the apical structure, wherein the helically-arranged fibers are enclosed within a cup-shaped sleeve, wherein the apical structure is rotatable relative to the basal structure and wherein the direct cardiac compression device is expandable from a collapsed state to an expanded state.

In some examples, removable release wires or release lines are engaged with the fasteners, wherein the basal structure and the apical structure are releasably attached to the fasteners so that, when the release wires or release lines are engaged with the fasteners, the direct cardiac compression device is attached to the delivery arms, and when the release wires or release lines are removed from the fasteners, the direct cardiac compression device can be disengaged from the delivery arms.

In some examples, the direct cardiac compression device is in a collapsed state and the direct cardiac compression device is positioned within the internal lumen of the delivery sheath.

In some examples, the direct cardiac compression device is self-expandable from a collapsed state to an expanded state.

In some examples, the delivery arms possess tension within the delivery sheath such that, upon exiting from a distal end of the delivery sheath, the tension converts the delivery arms to a curved shape, wherein distal ends of the delivery arms flair outwardly and away from each other.

In some examples, the medical delivery device further includes a motor housed within a motor housing and coupled to the apical structure of the direct cardiac compression device.

In some examples, the medical delivery device further includes a suture ring fitted around and sealed to the motor housing.

In some examples, the medical delivery device further includes a fluid seal around a motor shaft inside a distal end of the motor housing.

Some embodiments relate to a method of delivering a medical device to a subject including:
  inserting a distal end of the medical device delivery system through an incision in the skin of subject, and
  deploying a medical device engaged with the delivery arms of the medical delivery system to within the body of the subject.

In some examples, the medical device is a direct cardiac compression device coupled to a motor within a motor housing, wherein the method includes:
  moving the distal end of the medical delivery system through an incision in a pericardium below the heart apex of the subject,
  deploying the direct cardiac compression device and motor from the delivery sheath and around the heart intra-pericardium, and
  releasing the direct cardiac compression device and motor from the delivery arms, and
  removing the delivery system from the subject.

In some examples, the delivery arms are used to advance the direct cardiac compression device in its collapsed form out of the delivery system sheath and to guide, position, and hold the direct cardiac compression device around the heart of the subject.

In some examples, the direct cardiac compression device includes a basal structure and an apical structure, wherein the basal structure and/or the apical structure is/are secured to the heart by:
one or more active grip features that are activated by the delivery system, and/or
one or more passive grip features that engage with the epicardium.

In some examples, the method includes securing the direct cardiac compression device in position to the heart by a suture mechanism activated by the delivery system.

In some examples, the direct cardiac compression device includes a basal structure and an apical structure, wherein the method includes securing the basal structure to a rib, the sternum or another supporting point within the thoracic cavity.

In some examples, the direct cardiac compression device includes a basal structure and an apical structure, wherein the method comprises securing the basal structure to the epicardium of the heart by suturing.

In some examples, the suturing is carried out by a suture mechanism that is activated by the delivery system.

In some examples, the method includes suturing a suture ring around the motor housing of the motor to the pericardium to close the pericardial sac.

In some examples, a motor shaft of the motor rotates within the motor housing and wherein the housing does not rotate relative to the patient's tissue.

In some examples, the method includes securing the motor housing to a rib, the sternum or another supporting point within the thoracic cavity.

DETAILED DESCRIPTION

We disclose a percutaneous delivery system for a whole-heart assist device. When deployed, a sleeve of the whole-heart assist device externally wraps around a still-intact-heart and provides an additional pumping force via a helically-arranged mechanism coupled to the sleeve (U.S. Pat. Nos. 7,883,325; 8,794,937; and 9,656,009). Using the percutaneous delivery system, a whole-heart assist device is implantable using minimally invasive surgery, for example by accessing the heart through a small incision and by passing the delivery system through a rib space.

Percutaneous Delivery System

In one aspect, we disclose a delivery system designed to be internally loaded and reversibly coupled with a collapsed whole-heart assist device and motor. The delivery system is configured to be inserted into a subject. Advancement of the whole heart assist device and motor out from a distal end of the delivery system, followed by expansion of a sleeve and helically-arranged fibers of the cardiac assist device, opens up the sleeve so that it can be fit around the base of a heart. The whole-heart assist device may have grip features that grasp onto heart muscle tissue. Following deployment of the whole-heart assist device and motor, the delivery system is retracted from the subject, leaving the whole-heart assist device and motor in place.

Figure 1:
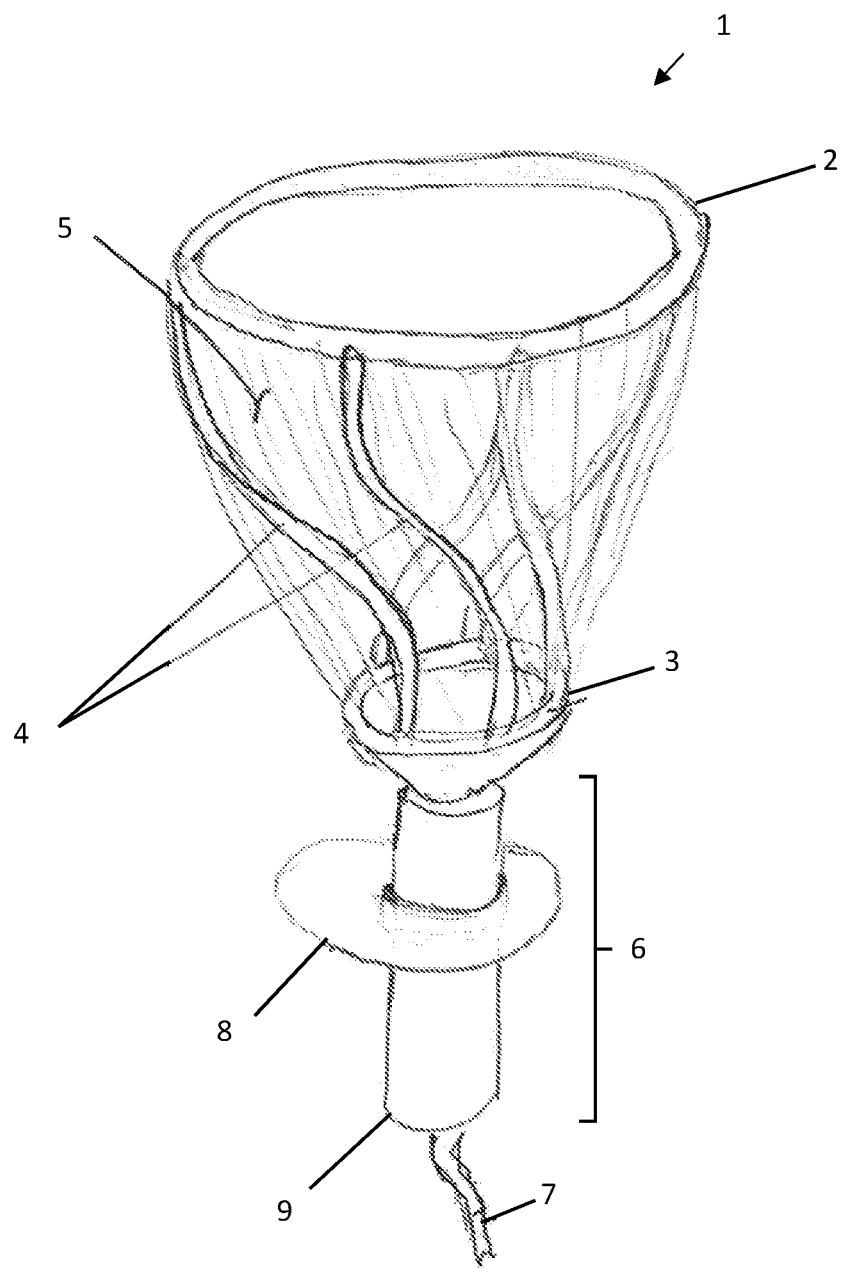
FIG. 1. A whole-heart assist device coupled to a motor.

Referring to FIG. 1, a whole heart assist device (1) is shown in an expanded conformation, including basal structure (2) and apical structure (3), interconnected to each other by helically-arranged fibers (4) that are enclosed within a sleeve (5), sized and configured to wrap around and engage with the base of a heart. A motor (6) is connected to the apical structure and is configured to be powered by motor power line (7). Suture ring (8), which can be sutured to the pericardium is fitted around and sealed to the motor housing (9).

Figure 2:
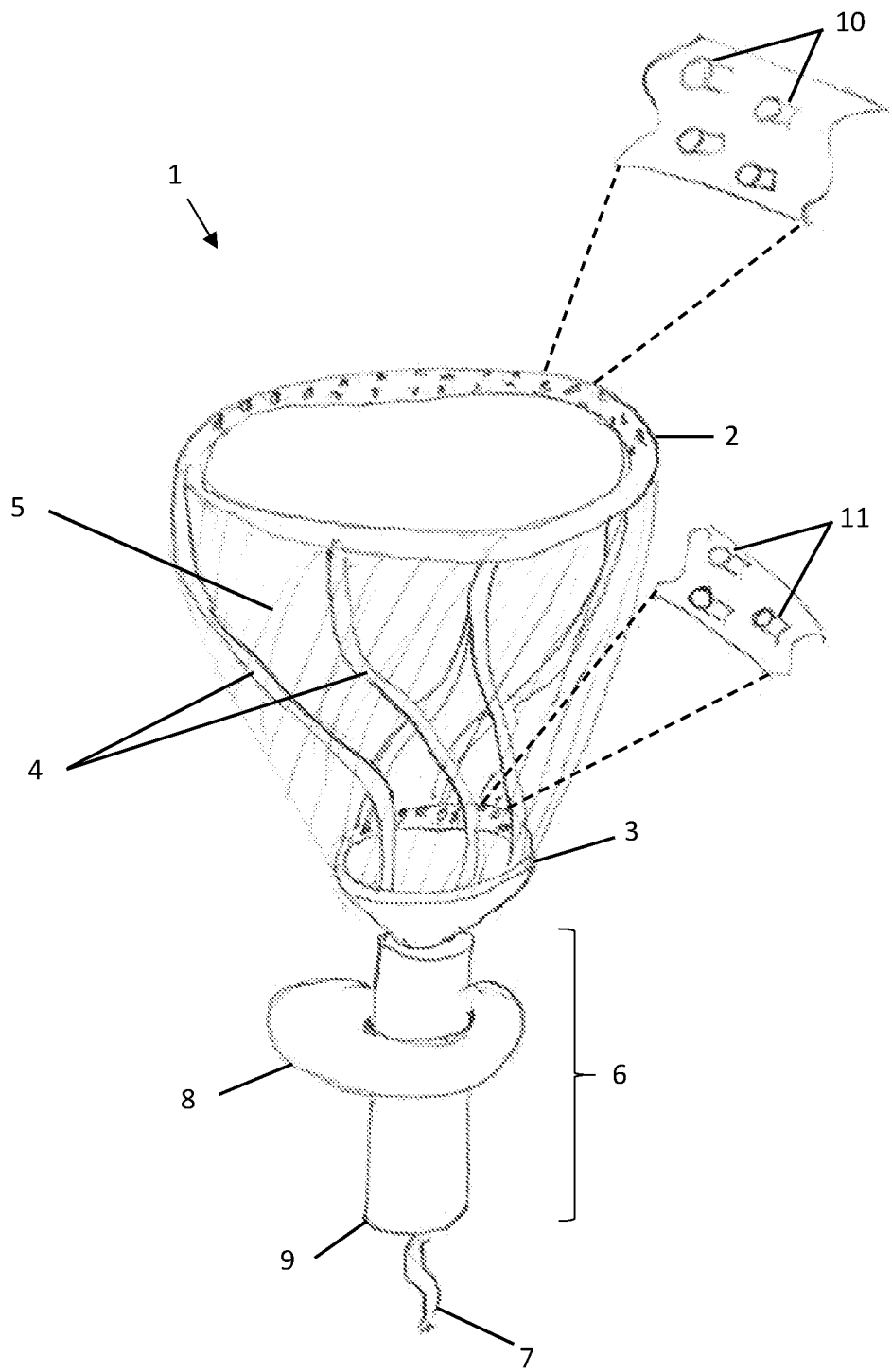
FIG. 2. A whole-heart assist device with basal and apical passive grip features.

Referring to FIG. 2, the whole-heart assist device may include basal passive grip features (10) and apical passive grip features (11), which may be in the shape of protrusions that engage with heart muscle to secure the basal and apical structures to the heart. The passive grip features may be any shape of projection, including cylindrical projections, pyramidal projections, and pillars, such as triangular, square, pentagonal and hexagonal pillars, as non-limiting examples.

Figure 3:
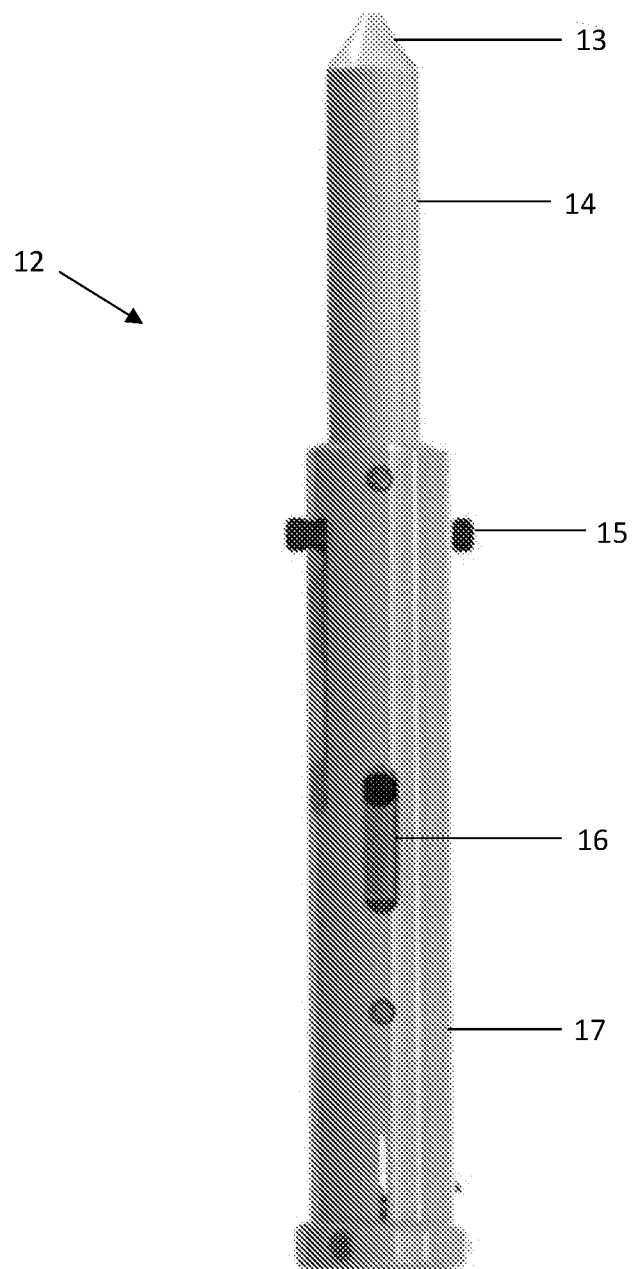
FIG. 3. A whole-heart assist device delivery system.

Referring to FIG. 3, the percutaneous whole-heart delivery system includes delivery sheath (14), optionally including a removable distal tip (13); delivery arm controls (15) that are engaged with delivery arms (not shown) that are housed within the delivery sheath and extend along a longitudinal axis of the delivery sheath; a release control (16) that is connected to a release wire (not shown); housing (17), through which the delivery sheath passes longitudinally and which includes the delivery arm controls, and the release control.

Figure 4:
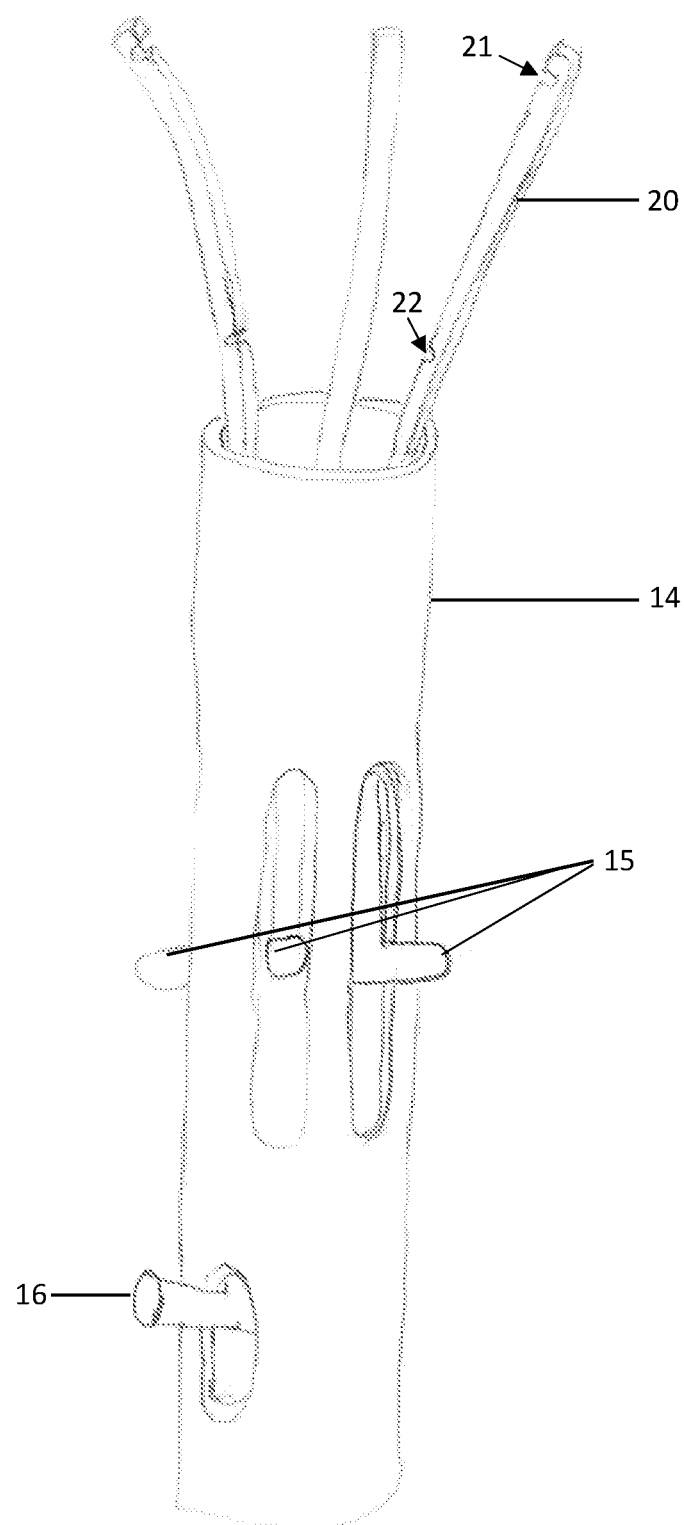
FIG. 4. A whole-heart assist device delivery system showing delivery arms, delivery sheath, delivery arm controls (with independent movement) and a release control.

FIG. 4 illustrates delivery arms (20) extending out from the distal end of delivery sheath (14) of a percutaneous whole-heart delivery system. The delivery arms include basal structure delivery arm fasteners, such as gaps or notches (21), and apical structure delivery arm fasteners, such as gaps or notches (22), configured to engage with basal structure and apical structures of the whole-heart assist device. Other embodiments may include knobs, hooks, clips or other types of fasteners configured to releasably attach the delivery arms to a whole-heart assist device. Delivery arm controls (15) (each having independent movement along a longitudinal axis of the delivery sheath) are used to advance the delivery arms out from the distal end of the delivery sheath. The deliver arms (a) may be flexible and able to bend outwardly along a longitudinal axis of the delivery sheath upon exiting the delivery sheath (for example to accommodate self-expanding helical fibers of the whole-heart assist device), or (b) the delivery arms may be curved so that when the delivery arms are housed within the delivery sheath, the arms possess tension. Upon exiting from the distal end of the delivery sheath, the tension returns the delivery arms to a curved shape and the delivery arms are configured to flair outwardly and away from each other. When engaged with a whole-heart assist device, the release of tension and a progressive outward curvature of the delivery arms opens up helical fibers and the sheath of the whole-heart assist device from a previously contracted conformation. In this configuration, the helical fibers of the whole-heart assist device need not be self-expanding. Release control (16), which is coupled to release wires (not shown) that extend longitudinally through each of the delivery arms, is used to pull and retract the release wires out from the delivery arms towards the release control.

Figure 5:
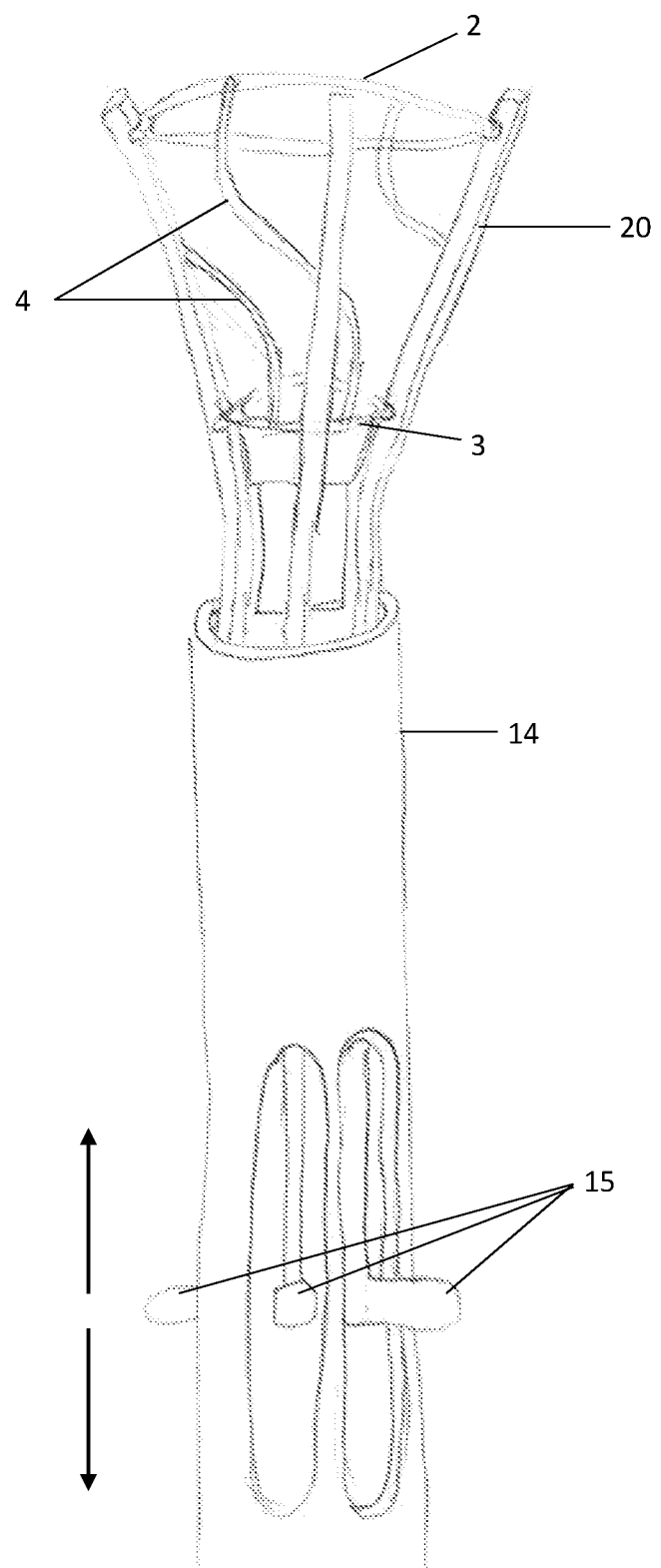
FIG. 5. A whole-heart assist device and motor loaded in a delivery system.

FIG. 5 depicts a whole-heart assist device engaged with the delivery arms of the delivery system. Basal structure (2) is engaged at distal ends of the delivery arms and apical structure (3) is engaged with an intermediate position of the delivery arms.

Figure 6:
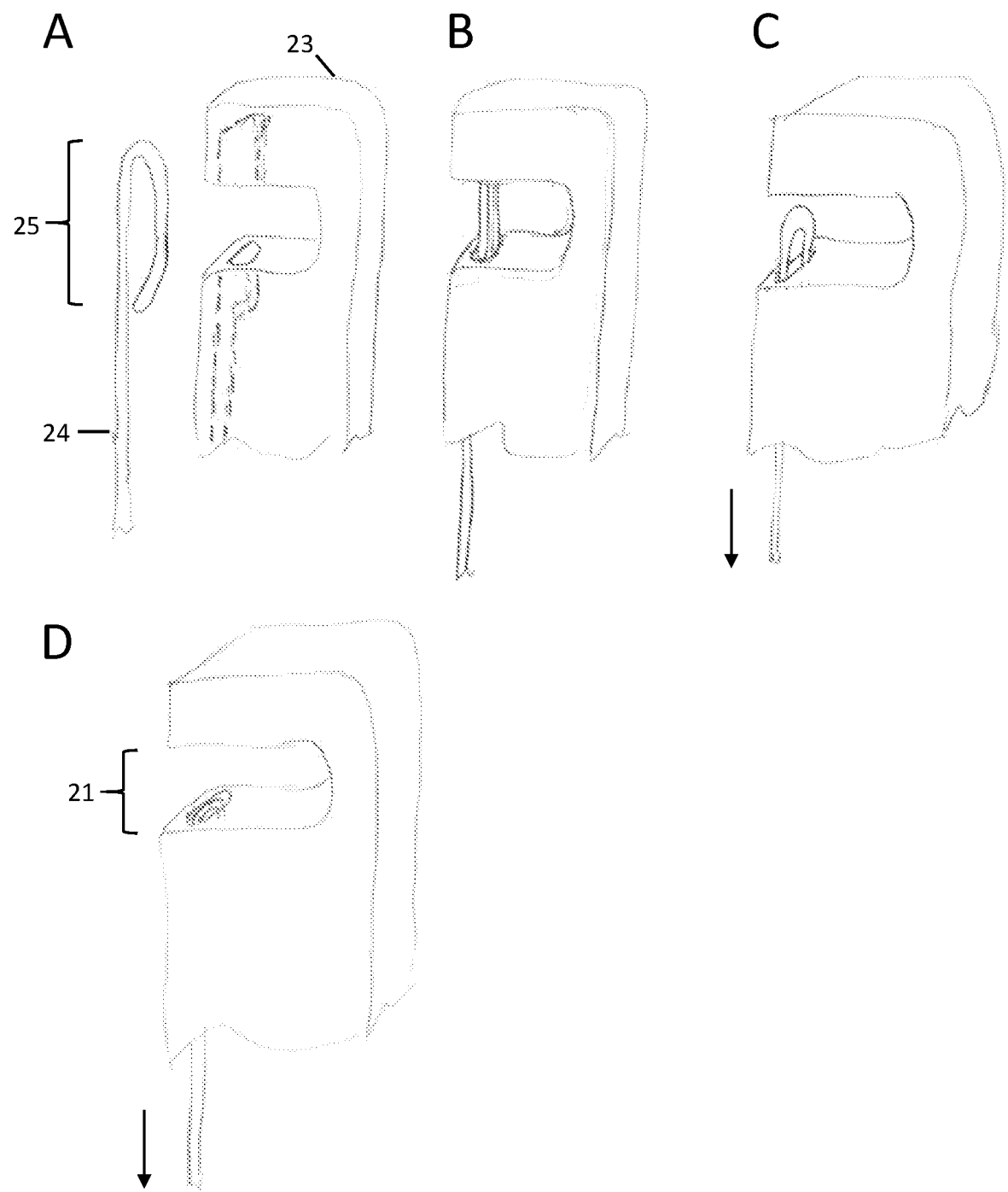
FIG. 6. (A)-(D) Fastener or clasping mechanism at distal end of delivery arms configured to engage with basal structure of whole heart assist device.

FIG. 6 shows a distal end (23) of a delivery arm (20) with a basal structure release mechanism including a basal structure delivery arm gap (21), a release wire (24) integrated within distal end of a delivery arm. These features constitute a release mechanism to release basal structure (2) from the delivery arm. (A) release wire (24), with release wire loop (25) are shown to the left side of the distal end of the delivery arm. (B) The release wire is positioned within a lumen of the delivery arm, with a distal portion of the wire formed into release wire loop (25). When the release wire is positioned distally, the loop extends across a delivery arm gap. (C) When the release wire is retracted, the loop is pulled proximal across the delivery arm gap. The basal structure is attached to the delivery arm by placing it within basal structure delivery arm gap (21) and then advancing the release wire distal across the gap and into a mating lumen in the delivery arm distal of the gap. The basal structure is released from the delivery arm by pulling the release wire proximal until the release wire had been pulled proximal of the basal structure delivery arm gap (21).

Figure 7:
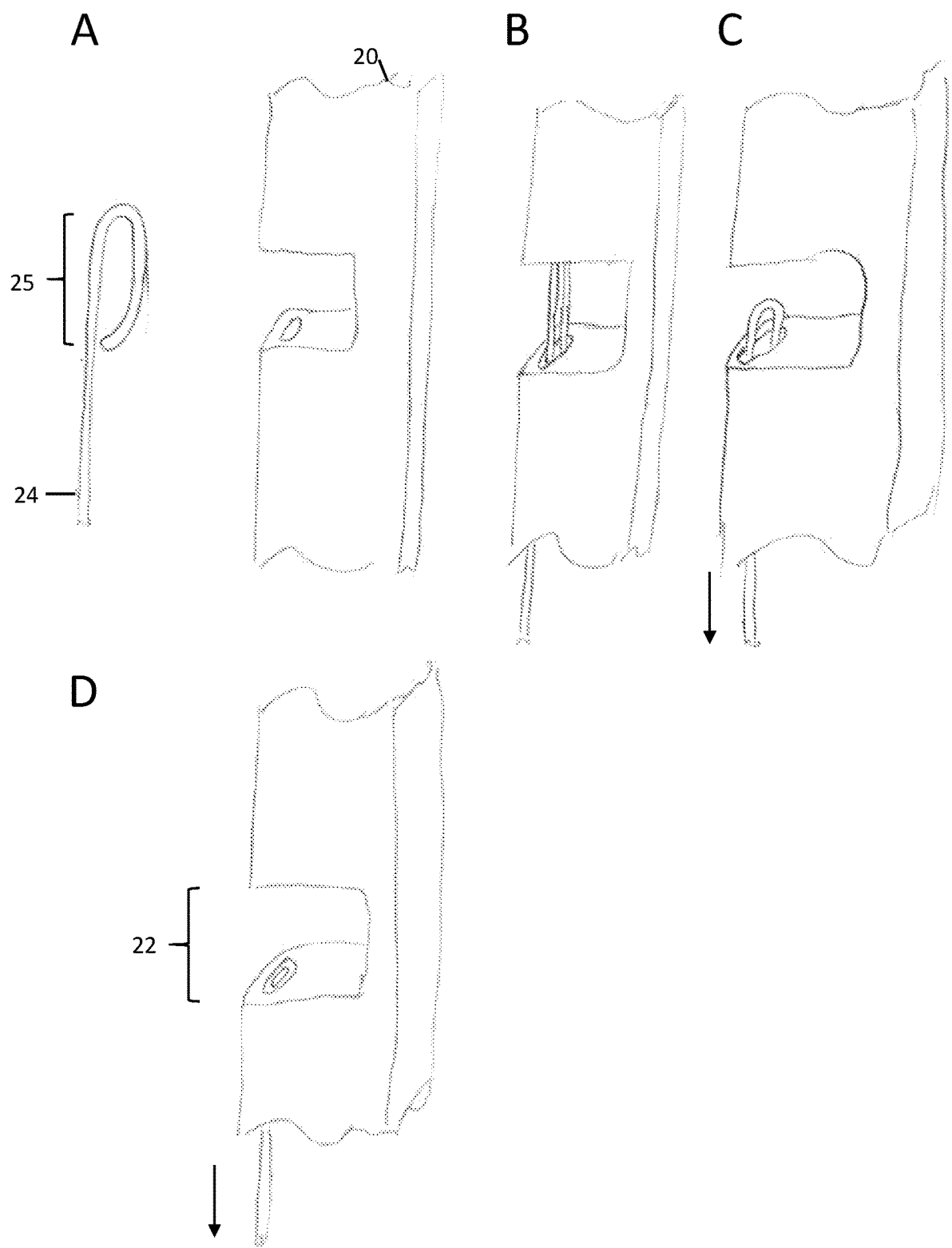
FIG. 7. (A)-(D) Fastener or clasping mechanism at an intermediate position of delivery arms configured to engage with apical structure of whole-heart assist device.

FIG. 7, shows an apical position of a delivery arm (20) a release wire (24) integrated within the apical position of a delivery arm (20). These features constitute a release mechanism to release apical structure (3) from the delivery arm. (A) Release wire (24), with release wire loop (25) are shown to the left side of the apical position of the delivery arm. (B) The release wire is positioned within a lumen of the delivery arm, with a distal portion of the wire formed into release wire loop (25). When release wire (24) is positioned distally, it extends across apical structure delivery arm gap (22). (C) When the wire is retracted the loop is pulled proximal across the apical structure delivery arm gap. The apical structure is attached to the delivery arm by placing it within apical structure delivery arm gap (22) and then advancing the release wire distal across the gap and into a mating lumen in the distal end of the delivery arm. The apical structure is released from the delivery arm by pulling the release wire proximal until the release wire had been pulled proximal of apical structure delivery arm gap (22).

Figure 8:
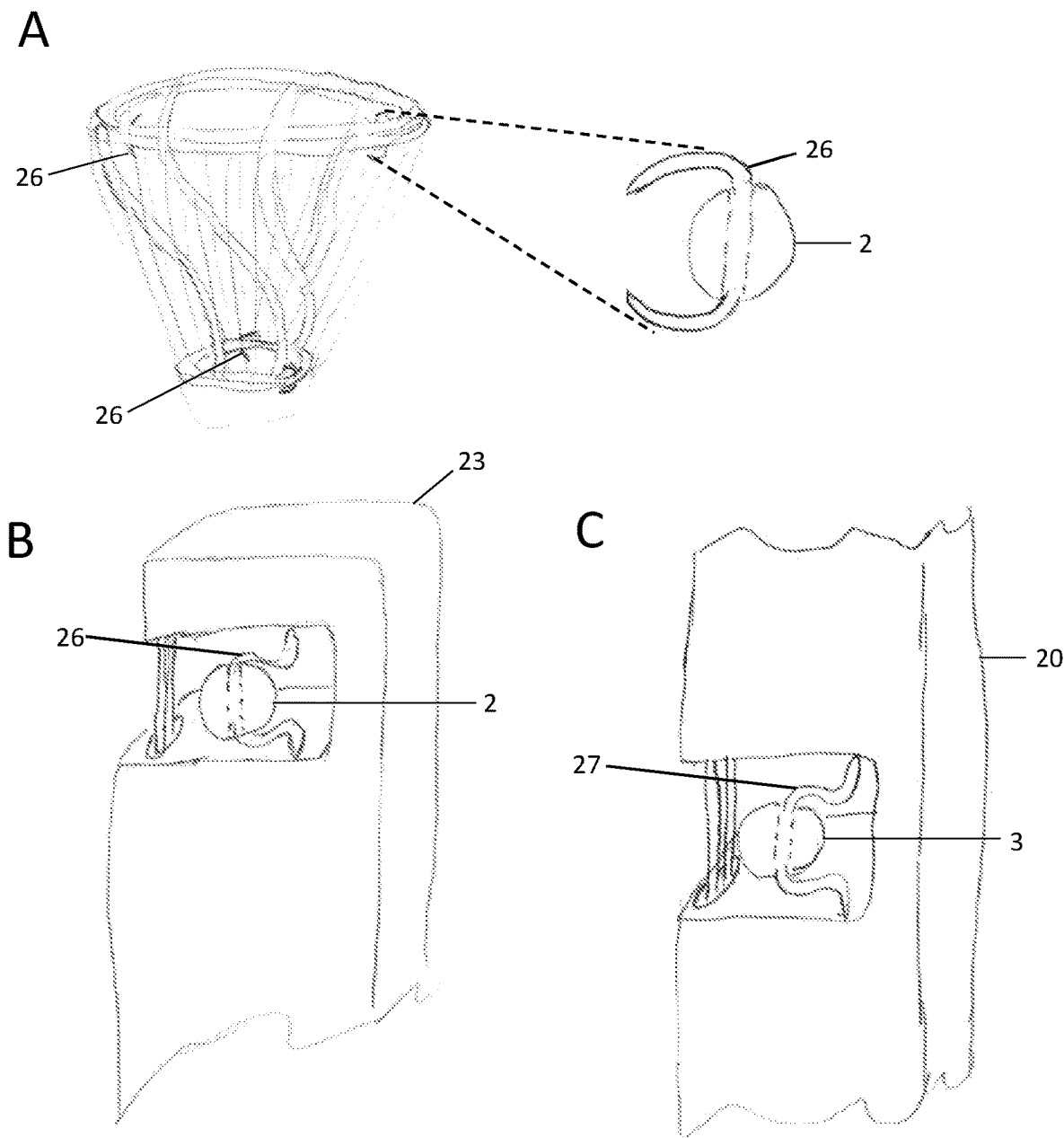
FIG. 8. (A)-(C) Active basal and apical grip features.

FIG. 8 shows active basal grip features (26) and active apical grip features (27). The grip features may be somewhat "C shaped" with sharp ends, which protrude beyond an inner surface of basal structure (2) and apical structure (3). The active grip features may be constructed in a configuration and of a material such that they may be elastically deformed in an open position, when the basal and apical structures are placed within corresponding delivery arm gaps, and they will elastically recover their shapes when released from the delivery arm gaps. With the basal and apical structures positioned around and against a heart, the sharp ends of the active grip features will penetrate into and grasp onto the heart muscle when the deformed grip feature springs closed after being released from the delivery arm gaps. (A) illustrates a whole-heart assist device (1), either prior to being loaded into a whole-heart device delivery system or when deployed. (B) A distal end (23) of a delivery arm showing active basal grip feature (26) in a deformed, open position when basal structure (2) is engaged in basal structure delivery arm gap (21). (C) An apical position of a delivery arm showing active apical grip feature (27) in a deformed, open position when apical structure (3) is engaged in apical structure delivery arm gap (22).

Figure 9:
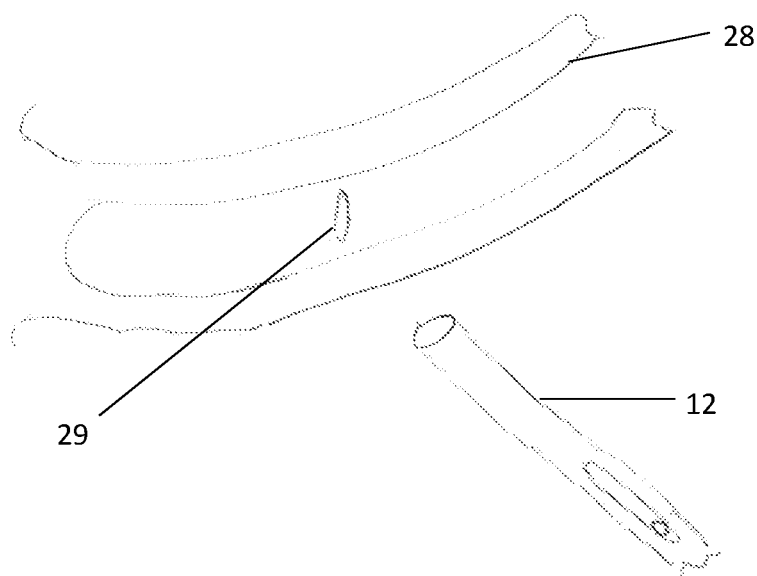
FIG. 9. (A)-(C) Implanting a whole-heart assist device and securing motor in a patient.
Figure 9:
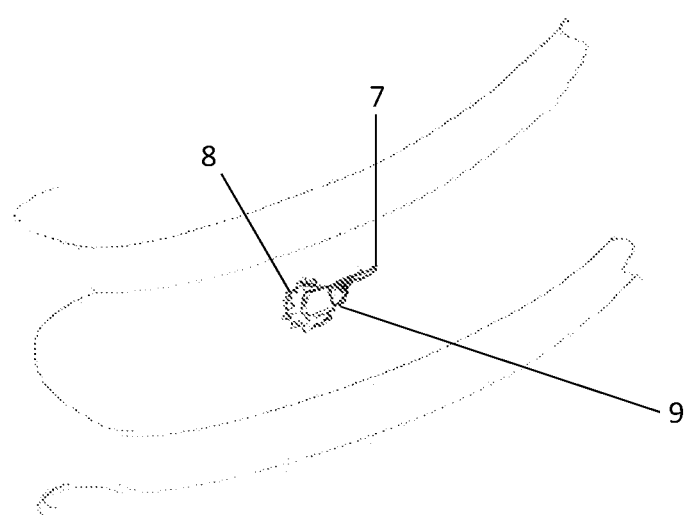
Figure 9:
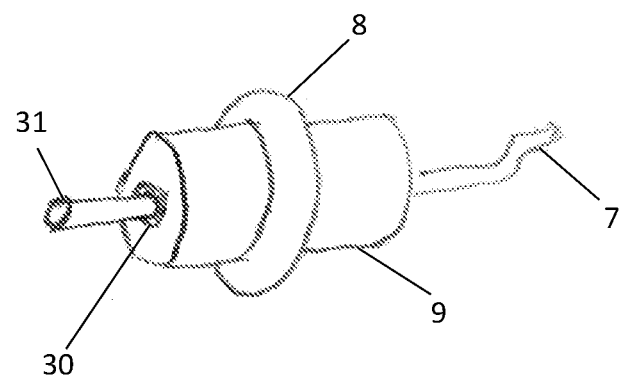

During implantation of a whole-heart assist device and motor into a patient, FIG. 9 shows placement of the delivery device between ribs of a subject and eventual placement of the motor. FIG. 9 (A) shows a whole-heart device delivery system (12), loaded with a whole-heart assist device and motor, ready to be inserted between a patient's ribs (28) and through an incision in the pericardial sac (29). FIG. 9 (B) shows the pericardial sac sutured to suture ring (8) around motor housing (9) to close the pericardial sac. FIG. 9 (C) shows a fluid seal (30) around the motor shaft (31) near the distal end of the motor housing.

Figure 10:
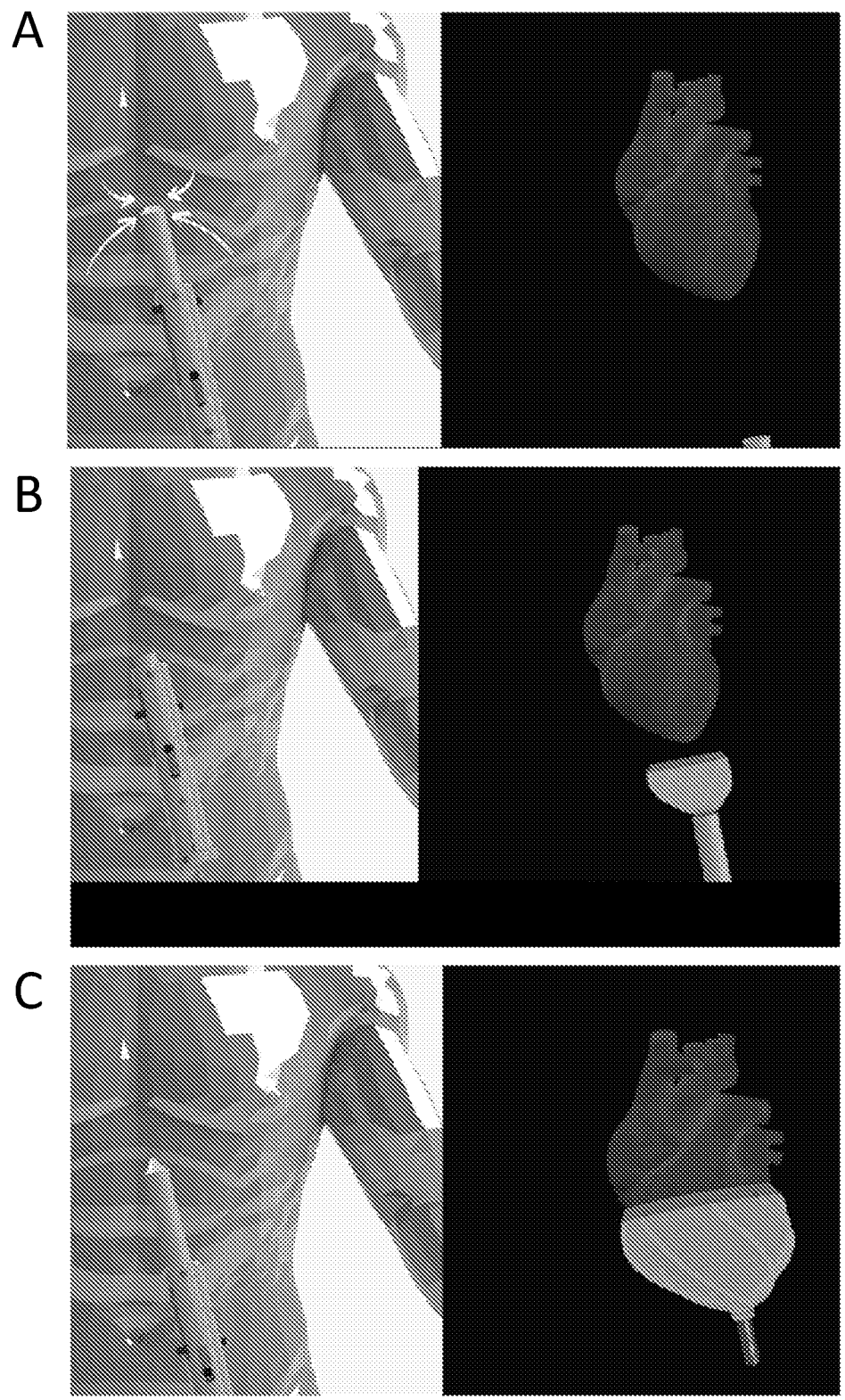
FIG. 10. (A)-(C) Stages of implanting a whole-heart assist device into a patient.

Referring to FIG. 10 (A), a whole-heart device delivery system is inserted into an incision in the pericardial sac (left), with whole-heart assist device and motor initially retracted and contained within the delivery system. As shown in FIG. 10 (B) during an intermediate stage during deployment of the whole-heart assist device and motor, the sleeve of the whole-heart assist device is partially opened near the base of a heart. As shown in FIG. 10 (C), following deployment and release of the whole-heart assist device and motor from the delivery system, with the sleeve surrounding the heart, the delivery device is withdrawn from the subject.

Figure 11:
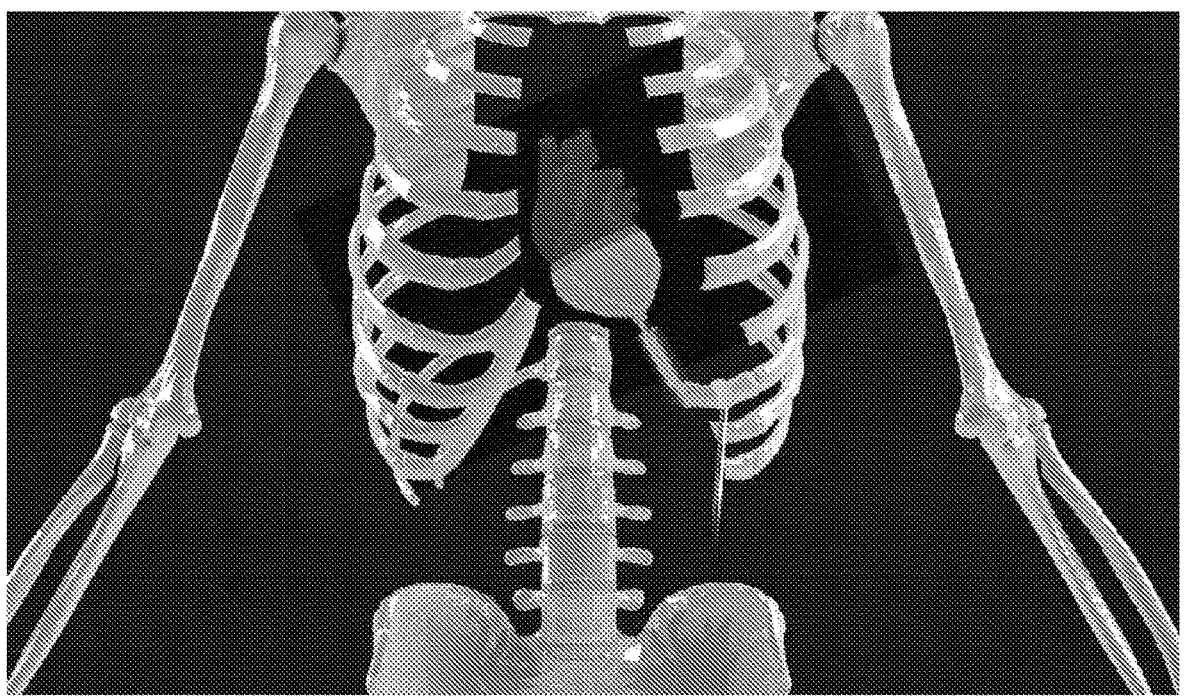
FIG. 11. Motor housing of whole-heart assist device secured to a rib, the sternum or another fixed point within the thoracic cavity, independent of the delivery system.
Figure 12:
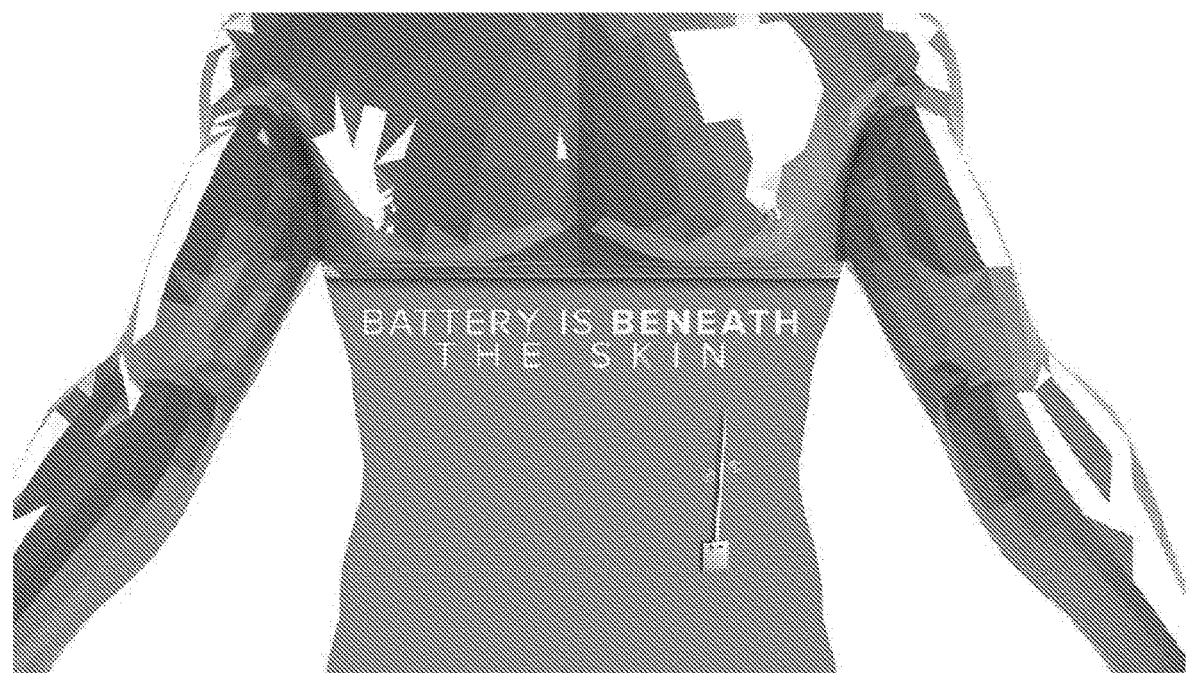
FIG. 12. Power source (e.g., a rechargeable battery) located beneath the skin.
Figure 13:
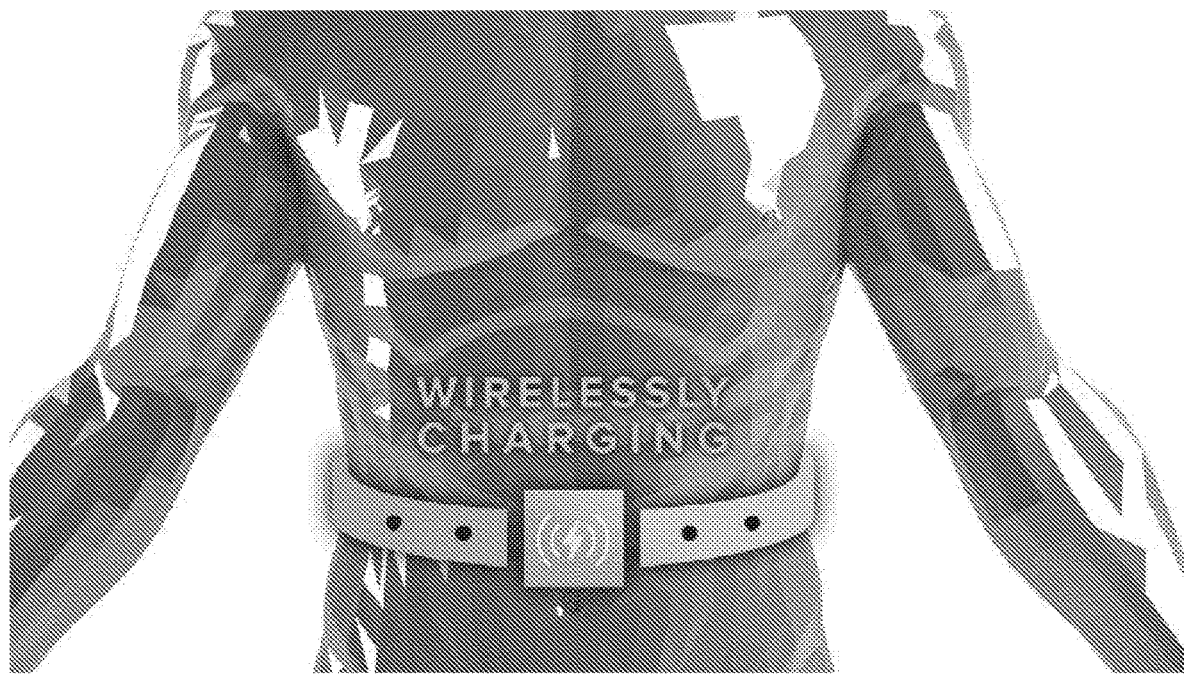
FIG. 13. Wireless charging of a rechargeable battery.

Following implantation, the whole-heart assist device may be secured to stationary anatomical features in the subject. For example, as shown in FIG. 11, the motor housing may be secured to a rib, the sternum or at another fixed position within the thoracic cavity, independent of the delivery system. To enable wireless internal power to the motor, a power source (e.g., a rechargeable battery) may be implanted and located beneath the skin, as illustrated in FIG. 12. In some embodiments, a rechargeable battery may be wirelessly recharged (FIG. 13), thereby avoiding disruptive and/or invasive charging.

Imaging Systems

The delivery system may be used in combination with an imaging modality that enables a physician to visualize the heart and the whole-heart assist device during an implantation surgery. For example, an imaging catheter may be extended through the delivery sheath of the delivery system to enable on-location visualization of the implantation procedure.

These imaging embodiments involve a catheter or catheter-like device that utilizes an integrated imaging modality with a deployment mechanism. As such, these embodiments may be used to accurately deploy a whole-heart assist device into a patient with great accuracy and precision. An imaging system allows the user to observe an image of the body cavity in which the whole-heart assist device is to be implanted.

In these embodiments, the delivery system incorporates a catheter-based imaging modality within the device, such as, but not limited to, intravascular ultrasound (IVUS), intravascular photoacoustic (IVP A) imaging, optical coherence tomography (OCT), an optoelectronic system or a fiber-optic system, raman spectroscopy, or an optical method, capable of detecting features of a vessel in which the catheter is inserted. The selected imaging systems allow clinicians to image both the surrounding anatomy and the advancing catheter and whole-heart assist device in real-time during an implantation procedure. In these embodiments, an image sensor or imaging head may be attached or secured to the distal end of the sleeve and the image or signal transfer cable (i.e., optical fiber, BNC cable, and the like) passes through the handle, through a lumen of the delivery sheath, and is connected (e.g., optically or electronically) to the image sensor or imaging head. The imaging system may be used independent of the delivery sheath.

In the example of IVUS hardware, a physician can accurately image and position the implantable whole-heart assist device without the use of ionizing radiation or nephrotoxic contrast agents. Furthermore. IVUS advantageously provides for a real-time imaging modality.

Operation of the delivery system allows visualization of the surrounding anatomy during insertion of the imaging catheter in the context of the location of the delivery sheath. As such, the location of the delivery sheath relative to the surrounding environment may always be known. In one embodiment, the delivery system is fixed relative to the imaging transducer within the catheter. In another embodiment, the two components can be moved relative to one another, wherein an imaging catheter having an associated imaging probe can be moved throughout the delivery sheath before, during and after implantation of a whole-heart assist device, for example.

Procedures for Implantation of Whole-Heart Assist Device with the Percutaneous Deliver System Using the percutaneous delivery system, a whole-heart assist device is implanted in a subject using minimally invasive surgery, where access to the heart is achieved through a small incision of the skin, rather than by using an "open" approach where inner organs or tissue are exposed. Minimally invasive heart surgery involves making a small incision, for example in the right side of the chest to reach the heart between the ribs, rather than cutting through the breastbone, as is done in open-heart surgery. Minimally invasive heart surgery can be performed to treat a variety of heart conditions. Compared with open-heart surgery, this type of surgery typically results in less pain, fewer complications and a quicker recovery for many people.

Prior to implantation of a whole-heart assist device, the whole-heart assist device is reversibly connected to the delivery system arms while the delivery arms are extended out from a delivery sheath. Various means may be used to reversibly attach the basal and apical structures of the whole heart assist to the delivery arms. In one embodiment, as depicted in FIG. 5, reversible connection to the delivery arms is achieved by attaching basal and apical structures of the whole-heart assist device with basal structure delivery arm gaps (21), and apical structure delivery arm gaps (22), configured to reversibly engage with the basal apical structures of the whole-heart assist device. The basal and apical structures are reversibly secured in place, for example by release wires integrated within delivery arms that are withdrawn in order to release the basal and apical structures from the delivery arms.

Once engaged with the delivery system arms, the motor and whole-heart assist device are loaded into the delivery system by retracting the delivery arms, with the attached collapsible helical fibers, sleeve and motor, into the delivery sheath of the delivery system.

During implantation, the delivery system is inserted between a patient's ribs and through an incision in the pericardium below the heart apex. The implantation procedure may be tracked using imaging modalities that enable visualization of the whole-heart assist device and the heart.

Once the distal end of the delivery sheath is brought into position below the heart apex, the whole-heart assist device is deployed from the delivery system. The delivery arms are slidably moved along the longitudinal axis of the delivery sheath, using delivery arm controls (15) (each having independent movement along a longitudinal axis of the delivery sheath) to advance the delivery arms out from the distal end of the delivery sheath and to guide, position, and hold the basal structure of the whole-heart assist device in position around the heart. In some embodiments, the deliver arms are flexible and able to bend outwardly along a longitudinal axis of the delivery sheath upon exiting the delivery sheath (for example to accommodate self-expanding helical fibers of the whole-heart assist device). In other embodiment, the delivery arms may be curved so that when the delivery arms are housed within the delivery sheath, the arms possess tension. Upon exiting from the distal end of the delivery sheath, the tension returns the delivery arms to a curved shape and the delivery arms are configured to flair outwardly and away from each other. When engaged with a whole-heart assist device, the release of tension and a progressive outward curvature of the delivery arms opens up helical fibers and the sheath of the whole-heart assist device from a previously contracted conformation. In this configuration, the helical fibers of the whole-heart assist device may or may not be self-expanding.

When the sleeve and associated helical fibers are positioned around the heart, the basal structure is secured to the heart. For example, the basal structure of the whole-heart assist device may have passive grip features which rest against and engage with the epicardium. The basal structure may have active grip features which may be activated by the delivery system. Both passive and active grip features are advantageously used to engage with the epicardium. The basal structure of the whole-heart assist device may also be secured in position to the heart by a suture mechanism activated by the delivery system. To stabilize the whole-heart assist device in place in the patient, the basal structure may be externally secured to a rib, the sternum or elsewhere within the thoracic cavity, independent of the delivery system. A strap or portion of the basal structure may be wrapped over the atrial area of the heart to secure the whole-heart assist device in position around the heart.

The apical structure is also secured to the heart apex. For example, the apical structure of the whole-heart assist device may have passive grip features which rest against and engage with the epicardium. The apical structure may have active grip features which may be activated by the delivery system. Both passive and active grip features are advantageously used to engage the apical structure with the epicardium. The apical structure of the whole-heart assist device may be secured in position to the heart by a suture mechanism activated by the delivery system.

Once the whole-heart assist device is deployed and secured around the heart, the whole-heart assist device is released from the delivery system and the delivery system is withdrawn through the small incision between the ribs.

To close the pericardial sac, the pericardium is sutured around the motor housing to close the pericardial sac. In some embodiments, a suture ring is fitted around and sealed to the motor housing and the pericardium is sutured to a suture ring. In some embodiments, there is a fluid seal around the motor shaft inside the distal end of the motor housing. During operation of the whole-heart assist device, the motor shaft rotates within the motor housing and the housing does not rotate relative to the patient's tissue. Independent of the delivery system, motor housing attachments may be sutured to a rib, the sternum or elsewhere within the thoracic cavity. A power source (e.g., a battery) for the motor is connected and secured subcutaneously. Finally, the access cite is sutured and closed.

Treatment of Heart Failure

Heart failure is a chronic, progressive condition in which the heart muscle is unable to pump enough blood to meet the body's needs for blood and oxygen. One type of heart failure is congestive heart failure (CHF), a progressive condition in which cardiac function deteriorates over time. It is most common among people 65 years or older, but practically anyone can be at risk as the causes of heart failure include everything from coronary artery disease, high blood pressure, and congenital heart defects to myocarditis, abnormal heart rhythms, valve disease, diabetes, and obesity. The most common symptoms of the disease include shortness of breath and fatigue, and it is often diagnosed via blood tests, electrocardiograms, echocardiograms, stress tests, coronary angiograms, and chest x-rays, CHF remains one of the most costly diseases in the industrialized world, both in terms of healthcare dollars and the loss of human life.

Cardiac transplantation is generally considered to be the best recourse for end-stage CHF patients, but this treatment option is not available to most patients as the number of donated hearts is restricted. Pharmacologic therapies can improve heart function in the short term and relieve the symptoms associated with CHF, but are unable to restore and maintain normal heart function over the long term. Therefore, cardiac assist devices (CADs) are often a useful solution for end-stage CHF patients.

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

All figures, tables, and appendices, as well as patents, applications, and publications, referred to above, are hereby incorporated by reference.

Some embodiments have been described in connection with the accompanying drawing. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the present inventions herein disclosed should not be limited by the particular disclosed embodiments described above. The limitations in the claims are to be interpreted broadly based on the language employed in the claims and not limited to the examples described in the present specification or during the prosecution of the application, which examples are to be construed as non-exclusive.

What is claimed is:

1. A delivery system configured to deliver a direct cardiac compression device into a thoracic cavity of a subject, the system comprising:
   a) a delivery sheath that comprises an internal lumen,
   b) a plurality of delivery arms contained within the internal lumen of the delivery sheath and extending along a longitudinal axis of the internal lumen of the delivery sheath, wherein distal ends of the delivery arms comprise fasteners configured to engage with basal and apical structures of the direct cardiac compression, wherein the delivery arms are attached to delivery arm controls that are configured to advance the delivery arms and the direct cardiac compression device attached thereto out from a distal end of the delivery sheath, and
   c) removable release wires or release lines configured to engage with the fasteners to hold the basal and apical structures of the direct cardiac compression device in place at the fasteners;
   wherein the direct cardiac compression device comprises:
      i) the apical structure and the basal structure which are parallel to each other and flexibly connected to each other by a plurality of helically-arranged fibers spanning between the basal structure and the apical structure, wherein the helically-arranged fibers are enclosed within a cup-shaped sleeve, wherein the apical structure is rotatable relative to the basal structure and wherein the direct cardiac compression device is expandable from a collapsed state to an expanded state, and
      ii) a motor housed within a motor housing and coupled to the apical structure of the direct cardiac compression device; wherein the motor housing comprises a suture ring fitted around and sealed to the motor housing.

2. The delivery system as in claim 1 wherein the removable release wires or the release lines are engaged with the fasteners, wherein the basal structure and the apical structure are releasably attached to the fasteners so that, when the release wires or release lines are engaged with the fasteners, the direct cardiac compression device is attached to the delivery arms, and when the release wires or the release lines are removed from the fasteners, the direct cardiac compression device can be disengaged from the delivery arms.

3. The delivery device according to claim 1, wherein when the direct cardiac compression device is in a collapsed state, the direct cardiac compression device is positioned within the internal lumen of the delivery sheath.

4. The delivery device system according to claim 1, wherein the direct cardiac compression device is self-expandable from a collapsed state to an expanded state.

5. The delivery device according to claim 1, wherein the delivery arms possess tension within the delivery sheath such that, upon exiting from the distal end of the delivery sheath, the tension converts the delivery arms to a curved shape, wherein the distal ends of the delivery arms flair outwardly and away from each other.

6. The device delivery system according to claim 1, further comprising a fluid seal around a motor shaft inside a distal end of the motor housing.

7. A method of delivering a direct cardiac compression device into a thoracic cavity of a subject, the method comprising:
   a) inserting a distal end of a delivery sheath of a delivery system configured to deliver a direct cardiac compression device through an incision in a pericardium below an apex of a heart in the skin of subject,
   wherein the delivery system comprises:
     i) the delivery sheath that comprises an internal lumen,
     ii) a plurality of delivery arms contained within the internal lumen of the delivery sheath and extending along a longitudinal axis of the internal lumen of the delivery sheath, wherein distal ends of the delivery arms comprise fasteners configured to engage with basal and apical structures of the direct cardiac compression device, and
     iii) removable release wires or release lines configured to engage with the fasteners to hold the basal and apical structures of the direct cardiac compression device in place at the fasteners;
   wherein the direct cardiac compression device comprises:
     i) the apical structure and the basal structure which are parallel to each other and flexibly connected to each other by a plurality of helically-arranged fibers spanning between the basal structure and the apical structure, wherein the helically-arranged fibers are enclosed within a cup-shaped sleeve, wherein the apical structure is rotatable relative to the basal structure and wherein the direct cardiac compression device is expandable from a collapsed state to an expanded state, and
     ii) a motor housed within a motor housing and coupled to the apical structure of the direct cardiac compression device; wherein the motor housing comprises a suture ring fitted around and sealed to the motor housing:
   b) deploying the direct cardiac compression device using the delivery arms of the delivery system from the distal end of the delivery sheath to around the heart intrapericardium; wherein the direct cardiac compression device is in the collapsed state within the delivery sheath and expands into the expanded state once deployed from the delivery sheath; and wherein the delivery arms quide, position, and hold the direct cardiac compression device in the expanded state around the heart;
   c) securing either the apical structure, the basal structure, or both to the heart;
   d) securing the suture ring of the motor housing to the pericardium to close the pericardial sac:
   e) releasing the direct cardiac compression device from the delivery arms, and
   f) removing the delivery system from the subject.

* * * * *